United States Patent
Wu et al.

(10) Patent No.: US 7,501,526 B2
(45) Date of Patent: Mar. 10, 2009

(54) SYNTHESIS OF POLYAMINE COMPOUNDS

(75) Inventors: Chien-Huang Wu, Taipei County (TW); Jia-Liang Zhu, Taipei (TW); Chen-Tso Tseng, Taipei (TW); Chi-Feng Yen, Taipei (TW); Kak-Shan Shia, Taipei (TW); Yibin Xiang, Acton, MA (US); Gholam Hossein Hakimelahi, Taipei (TW); Ming-Chen Chou, Taipei (TW)

(73) Assignee: Taigen Biotechnology, Taipei (TW)

( * ) Notice: Subject to any disclaimer, the term of this patent is extended or adjusted under 35 U.S.C. 154(b) by 360 days.

(21) Appl. No.: 11/039,283

(22) Filed: Jan. 20, 2005

(65) Prior Publication Data

US 2006/0160860 A1      Jul. 20, 2006

(51) Int. Cl.
*C07D 235/06*    (2006.01)
*C07D 235/10*    (2006.01)

(52) U.S. Cl. ............................. 548/309.7; 548/310.4

(58) Field of Classification Search ............... 548/309.7, 548/310.4
See application file for complete search history.

(56) References Cited

U.S. PATENT DOCUMENTS

| | | | |
|---|---|---|---|
| 5,252,317 A | 10/1993 | Keana | |
| 5,567,411 A | 10/1996 | Keana et al. | |
| 5,719,193 A | 2/1998 | Bowlin et al. | |
| 5,910,513 A | 6/1999 | Galey | |
| 2005/0043366 A1 | 2/2005 | Shia et al. | |

FOREIGN PATENT DOCUMENTS

| | | |
|---|---|---|
| JP | 62129858 A | 6/1987 |
| JP | 64-66117 | 3/1989 |
| JP | 1-272568 | 10/1989 |
| JP | 2002-543126 | 12/2002 |
| JP | 3714948 | 9/2005 |
| WO | WO 97/00245 | 1/1997 |
| WO | WO 00/02870 | 1/2000 |
| WO | WO 00/56729 | 9/2000 |
| WO | WO 00/66112 | 11/2000 |
| WO | WO 02/22600 A2 | 3/2002 |
| WO | WO 02/055112 A2 | 7/2002 |
| WO | WO 02/083143 A1 | 10/2002 |
| WO | WO2004/089360 | 10/2004 |

OTHER PUBLICATIONS

Mohamadou et al., "Synthesis and Characterisation of Zinc(II) Complexes of Tripodal N7 Ligands Involving Pyridine and Amine or Amide Nitrogen Donors. Crystal Structure of a Zine (II) Complex", J. Chem. Soc., Dalton Trans., 3320-3328, 2001.
Rannard et al., "The Selective Reaction of Primary Amines with Carbonyl Imidazole Containing Compounds: Selective Amide and Carbamate Synthesis", Org. Lett., 2:2117-2120, 2000.
Xu et al., "Specific Sequestering Agents for the Actinides. 28. Synthesis and Initial evaluation of Multidentate 4-Crabamoyl-3-hydroxy-1-methyl-2(1H)-pyridinone Ligands for in Vivo Plutonium (IV) Chelation", J. Med. Chem. 38:2606-2614, 1995.
Yu et al., "Study on Antioxidative Succinimide Dispersants," *Chemical Abstracts Service*, [Online] XP002452292, Abstract.
Tecilla et al., "Acceleration o p-Nitrophenyl Ester Cleavage by Zn (II)- Organized Molecular Receptors," *Journal of Organic Chemistry*, vol. 62 pp. 7621-7628 (1997) XP002452260.
Deroche et al., "A seven-Coordinate Manganese (II) Complex Formed with a Single Tripodal Heptadentate Ligand as a new Superoxide Scavenger," *Journal of the American Chemical Society*, vol. 118, No. 19, pp. 4567-4573 (1996) XP002452261.
Wuntz et al., J. Med. Chem., vol. 33, No. 6, pp. 1549-1553, (1990).

*Primary Examiner*—James O. Wilson
*Assistant Examiner*—Ebenezer Sackey
(74) *Attorney, Agent, or Firm*—Occhiuti Rohlicek & Tsao LLP

(57) ABSTRACT

This invention relates to methods of preparing the compounds of formula (V):

(V)

[Chemical structure of formula (V) showing a polyamine compound with R₁, R₂, R₄, R₅, R₆ substituents and a benzimidazole moiety]

Each variable in this formula is defined in the specification.

19 Claims, No Drawings

SYNTHESIS OF POLYAMINE COMPOUNDS

BACKGROUND

Chemokines are a family of cytokines that regulate the adhesion and transendothelial migration of leukocytes during an immune or inflammatory reaction (Mackay C. R., Nat. Immunol., (2001) 2:95; Olson et al., Am. J. Physiol. Regul. Integr. Comp. Physiol., (2002) 283:R7). Chemokines also regulate T cells and B cells trafficking and homing, and contribute to the development of lymphopoietic and hematopoietic systems (Ajuebor et al., Biochem. Pharmacol., (2002) 63:1191). Approximately 50 chemokines have been identified in humans. They can be classified into 4 subfamilies, i.e., CXC, CX3C, CC, and C chemokines, based on the positions of the conserved cysteine residues at the N-terminal (Onuffer et al., Trends Pharmacol Sci., (2002) 23:459). The biological functions of chemokines are mediated by their binding and activation of G protein-coupled receptors (GPCRs) on the cell surface. Take CXCR4 receptor for example, it can be activated by Stromal-derived factor-1 or SDF-1, a member of CXC chemokines.

SDF-1 was originally cloned from bone marrow stromal cell lines and found to act as a growth factor for progenitor B cells (Nishikawa et al., Eur. J. Immunol., (1988) 18:1767). SDF-1 also induces bone marrow colonization of hematopoietic precursor cells during embryogenesis (Bleul et al., J. Exp. Med., (1996) 184:1101). The physiological function of SDF-1 is mediated by CXCR4 receptor. Mice lacking SDF-1 or CXCR4 receptor show lethal abnormality in bone marrow myelopoiesis, B cell lymphopoiesis, and cerebellar development (Nagasawa et al., Nature, (1996) 382:635; Ma et al., Proc. Natl. Acad. Sci., (1998) 95:9448; Zou et al., Nature (1998) 393:595; Lu et al., Proc. Natl. Acad. Sci. (2002) 99:7090). CXCR4 receptor is expressed broadly in a variety of tissues, particularly in immune and central nervous systems, and has been described as the major co-receptor for HIV-1/2 on T lymphocytes. Although initial interest in CXCR4 antagonism focused on its potential application to AIDS treatment (Bleul et al., Nature (1996) 382:829), it is now becoming clear that CXCR4 receptor and SDF-1 are also involved in other pathological conditions such as rheumatoid arthritis, asthma, and tumor metastases (Buckley et al., J. Immunol., (2000) 165:3423). CXCR4 receptor and SDF-1 are also found widely expressed in many tissues during embryonic development. Further, the CXCR4/SDF-1 pathway has been shown to be critically involved in the regeneration of several tissue injury models. Specifically, it has been found that the SDF-1 level is elevated at an injured site and CXCR4-positive cells actively participate in the tissue regenerating process.

Thus, it is desirable to develop drugs that are effective in treating the above-mentioned diseases by binding to chemokine receptors.

SUMMARY

This invention relates to processes of preparing therapeutic polyamine compounds. These compounds are effective in treating inflammatory and immune diseases, developmental or degenerative diseases, or tissue injuries through their binding to chemokine receptors (e.g., CXCR3 or CXCR4 receptors).

In one aspect, this invention features a chemical synthetic method. The method includes reacting a compound of formula (I):

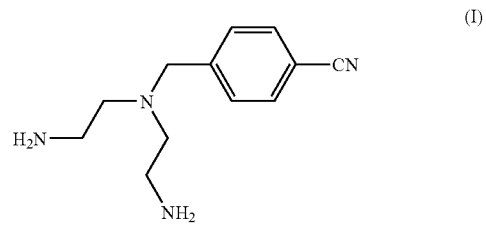

with $R_1$CHO to give a first imine compound, followed by reducing the first imine compound to give a compound of formula (II):

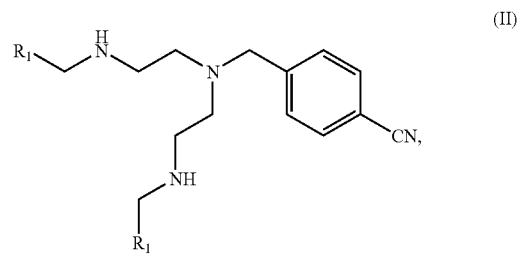

in which $R_1$ is heteroaryl, aryl, $C_3$-$C_8$ cycloalkyl, or $C_3$-$C_8$ heterocycloalkyl.

In particular, the chemical synthetic method can further include reducing the compound of formula (II) to an aldehyde compound, followed by reacting the aldehyde compound with an amino-protecting agent to give a compound of formula (III):

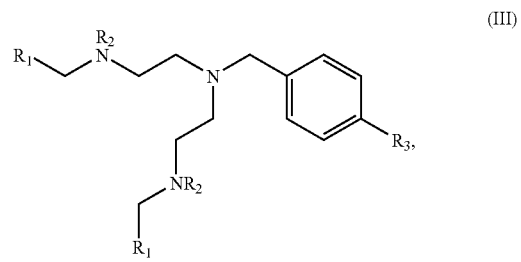

in which $R_2$ is an amino-protecting group and $R_3$ is C(O)H. In formulas (II) and (III), $R_1$ can be heteroaryl (e.g., pyridyl). In formula (III), $R_2$ can be t-butoxycarbonyl, benzyloxycarbonyl, acetyl, phenylcarbonyl, or trialkylsilyl. The compound of formula (III) can further react with a compound of formula (IV):

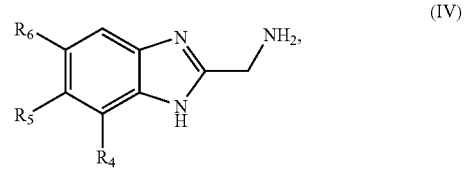

to give a second imine compound, followed by reducing the second imine compound to give a compound of formula (V):

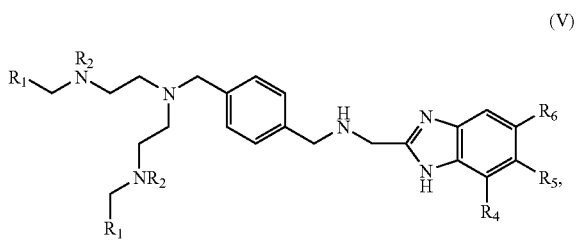

(V)

in which each of $R_4$, $R_5$, and $R_6$, independently, is H, OR', halogen, $C_1$-$C_{10}$ alkyl, $C_3$-$C_8$ cycloalkyl, $C_3$-$C_8$ heterocycloalkyl, aryl, or heteroaryl; and R' is H, $C_1$-$C_{10}$ alkyl, $C_3$-$C_8$ cycloalkyl, $C_3$-$C_8$ heterocycloalkyl, aryl, or heteroaryl. In formulas (IV) and (V), $R_4$, $R_5$, and $R_6$ can be H, OR', or halogen.

Alternatively, the chemical synthetic method can further include reducing the compound of formula (II) to give a compound of formula (III), in which $R_2$ is H and $R_3$ is $CH_2NH_2$. In the just-mentioned formula (III), $R_1$ can be heteroaryl (e.g., pyridyl). The compound of just-mentioned formula (III) can further react with a compound of formula (VI):

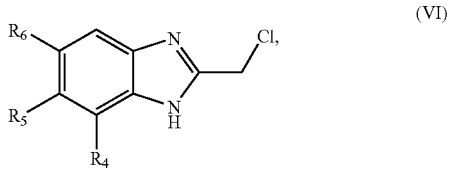

(VI)

to give a compound of formula (V), in which each of $R_4$, $R_5$, and $R_6$, independently, is H, OR', halogen, $C_1$-$C_{10}$ alkyl, $C_3$-$C_8$ cycloalkyl, $C_3$-$C_8$ heterocycloalkyl, heteroaryl, or aryl; and R' is H, $C_1$-$C_{10}$ alkyl, $C_3$-$C_8$ cycloalkyl, $C_3$-$C_8$ heterocycloalkyl, aryl, or heteroaryl. In the just-mentioned formulas (V) and (VI), $R_4$, $R_5$, and $R_6$ can be H, OR', or halogen.

The term "alkyl" refers to a saturated or unsaturated, linear or branched, non-aromatic hydrocarbon moiety, such as —$CH_3$, —$CH_2$—, —$CH_2$—CH=$CH_2$—, or branched —$C_3H_7$. The term "cycloalkyl" refers to a saturated or unsaturated, non-aromatic, cyclic hydrocarbon moiety, such as cyclohexyl or cyclohexen-3-yl. The term "heterocycloalkyl" refers to a saturated or unsaturated, non-aromatic, cyclic moiety having at least one ring heteroatom, such as 4-tetrahydropyranyl or 4-pyranyl. The term "aryl" refers to a hydrocarbon moiety having one or more aromatic rings. Examples of an aryl moiety include phenyl, phenylene, naphthyl, naphthylene, pyrenyl, anthryl, and phenanthryl. The term "heteroaryl" refers to a moiety having one or more aromatic rings that contain at least one heteroatom. Examples of a heteroaryl moiety include furyl, flirylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, cycloalkyl, heterocycloalkyl, aryl, and heteroaryl mentioned herein include both substituted and unsubstituted moieties, unless specified otherwise. Examples of substituents on cycloalkyl, heterocycloalkyl, aryl, and heteroaryl include $C_1$-$C_{10}$ alkyl, $C_2$-$C_{10}$ alkenyl, $C_2$-$C_{10}$ alkynyl, $C_3$-$C_8$ cycloalkyl, $C_5$-$C_8$ cycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, hydroxyl, halogen, thio, $C_1$-$C_{10}$ alkylthio, arylthio, $C_1$-$C_{10}$ alkylsulfonyl, arylsulfonyl, cyano, nitro, acyl, acyloxy, carboxyl, and carboxylic ester. On the other hand, examples of substituents on alkyl include all of the above-recited substituents except $C_1$-$C_{10}$ alkyl, $C_2$-$C_{10}$ alkenyl, and $C_2$-$C_{10}$ alkynyl. Cycloalkyl, heterocycloalkyl, aryl, and heteroaryl also include fused groups.

In another aspect, the invention features a compound of formula (III), in which $R_1$ is heteroaryl, aryl, $C_3$-$C_8$ cycloalkyl, or $C_3$-$C_8$ heterocycloalkyl; $R_2$ is H or an amino-protecting group; and $R_3$ is CN, C(O)H, or $CH_2NH_2$.

Referring to formula (III), a subset of the just-described compounds are those in which $R_1$ is heteroaryl (e.g., pyridyl) and $R_2$ is H, t-butoxycarbonyl, benzyloxycarbonyl, acetyl, phenylcarbonyl, or trialkylsilyl. Exemplary compounds of formula (III) include:

Compound 1

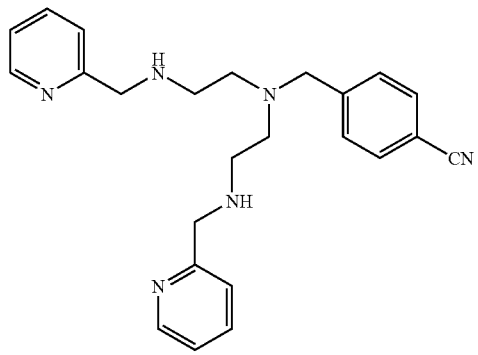

Compound 2

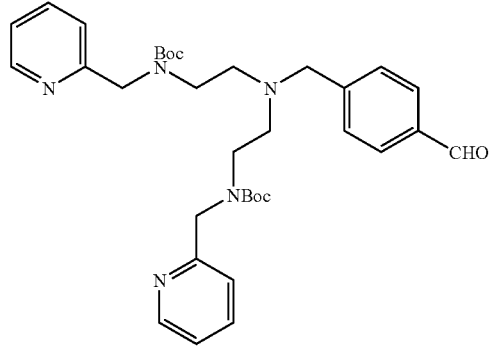

Compound 3

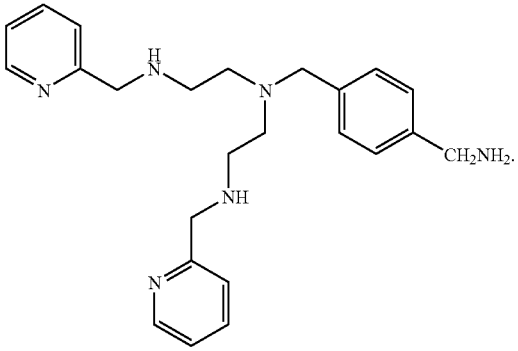

In a further aspect, this invention features a compound of formula (V), in which $R_1$ is heteroaryl, aryl, $C_3$-$C_8$ cycloalkyl, or $C_3$-$C_8$ heterocycloalkyl; $R_2$ is H or an amino-protecting group; and each of $R_4$, $R_5$, and $R_6$, independently, is H, OR', halogen, $C_1$-$C_{10}$ alkyl, $C_3$-$C_8$ cycloalkyl, $C_3$-$C_8$ heterocycloalkyl, heteroaryl, or aryl; R' being H, $C_1$-$C_{10}$ alkyl, $C_3$-$C_8$ cycloalkyl, $C_3$-$C_8$ heterocycloalkyl, aryl, or heteroaryl.

Referring to formula (V), a subset of the just-described compounds are those in which $R_1$ is heteroaryl (e.g., pyridyl); $R_2$ is H, t-butoxycarbonyl, benzyloxycarbonyl, acetyl, phenylcarbonyl, or trialkylsilyl; and each of $R_4$, $R_5$, and $R_6$, independently, is H, OR', or halogen. Shown below are the exemplary compounds of formula (V):

Compound 4

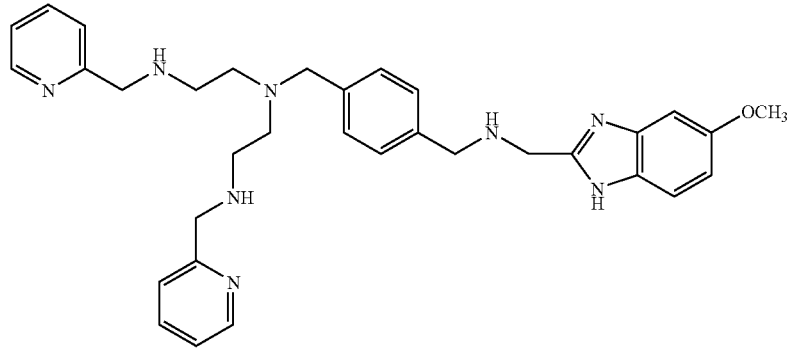

Compound 5

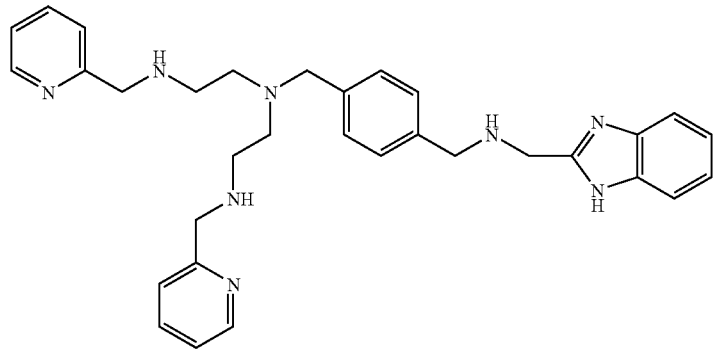

Compound 6

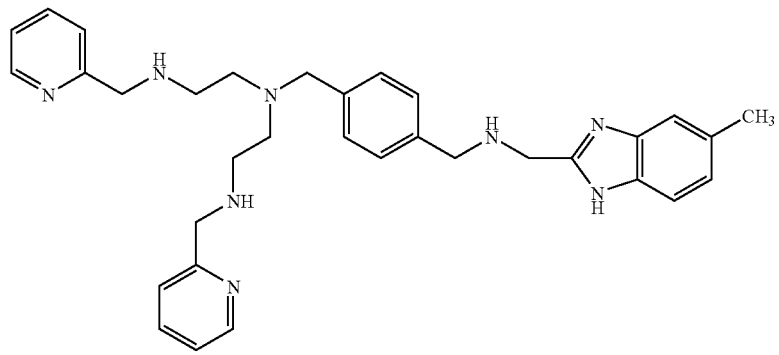

Compound 7

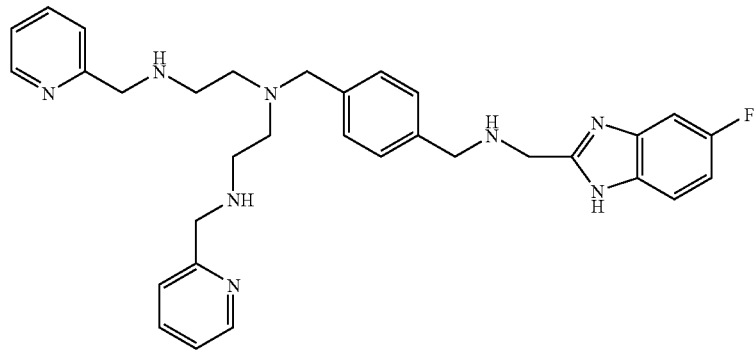

-continued
Compound 8
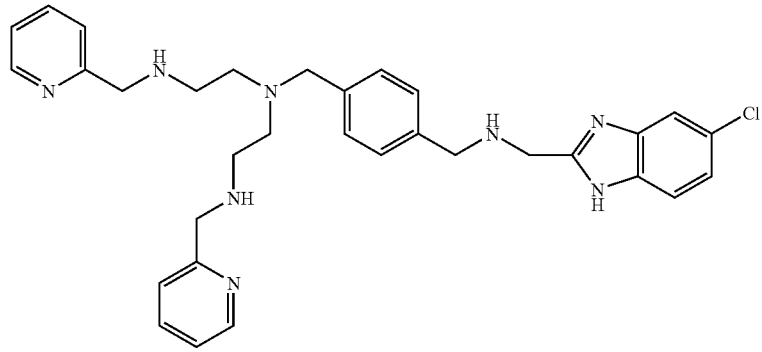
Compound 9
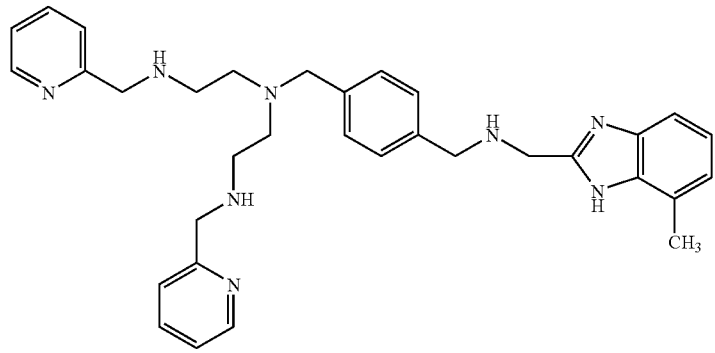
Compound 10
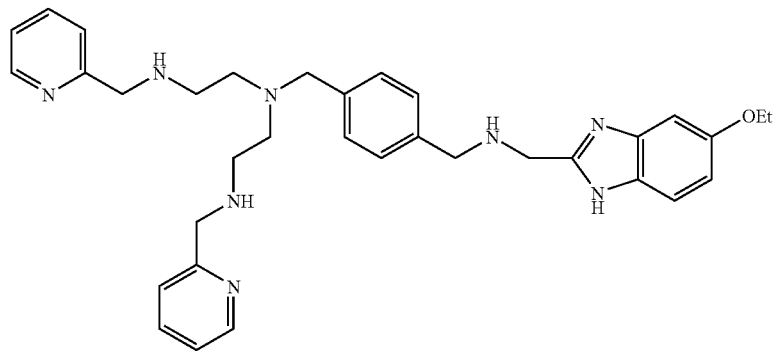
Compound 11
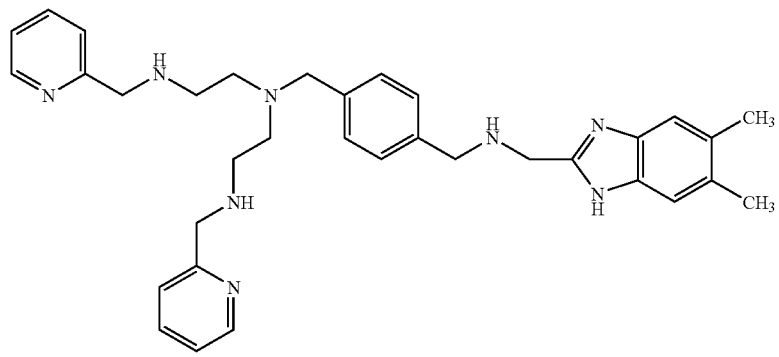

-continued

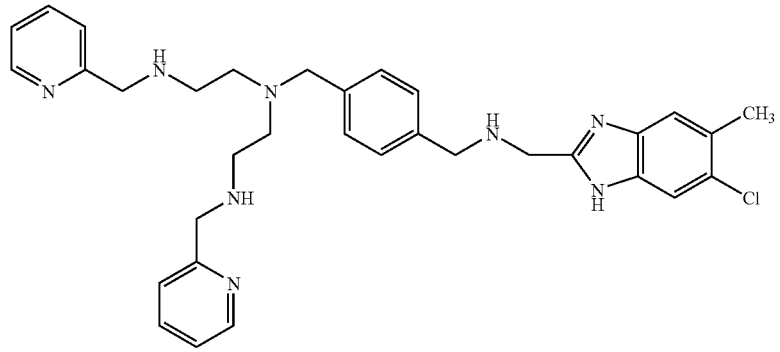

Compound 12

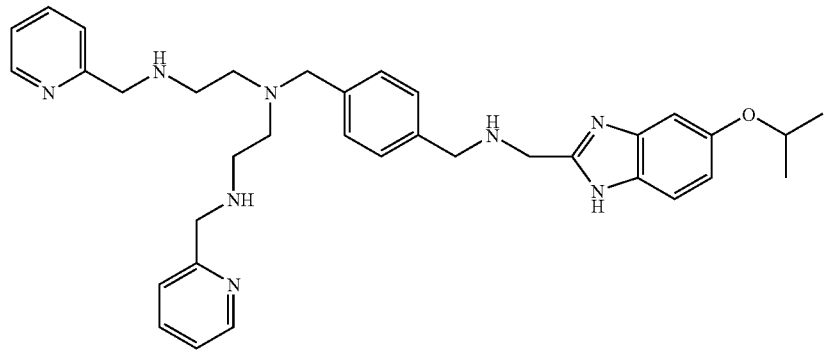

Compound 13

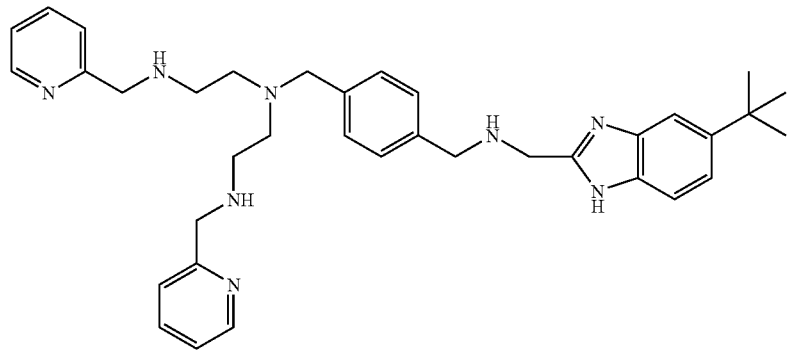

Compound 14

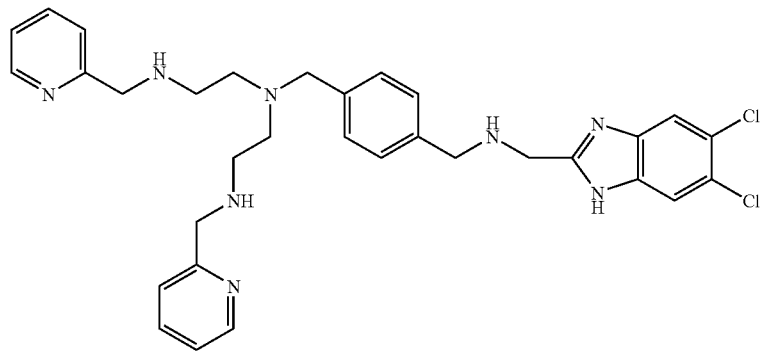

Compound 15

In addition, this invention encompasses a pharmaceutical composition that contains an effective amount of at least one of the above-mentioned polyamine compounds and a pharmaceutically acceptable carrier.

The polyamine compounds described above include the compounds themselves, as well as their salts, prodrugs, and solvates, if applicable. A salt, for example, can be formed between an anion and a positively charged group (e.g., amino) on a polyamine compound. Examples of suitable anions include chloride, bromide, iodide, sulfate, nitrate, phosphate, citrate, methanesulfonate, trifluoroacetate, and acetate. Likewise, a salt can also be formed between a cation and a negatively charged group (e.g., carboxylate) on a polyamine compound. Examples of suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active polyamine compounds. A solvate refers to a complex formed between an active polyamine compound and a pharmaceutically acceptable solvent. Examples of pharmaceutically acceptable solvents include water, ethanol, isopropanol, ethyl acetate, acetic acid, and ethanolamine.

Also within the scope of this invention is a composition containing one or more of the polyamine compounds described above for use in treating inflammatory and immune diseases, developmental or degenerative diseases, or tissue injuries, and the use of such a composition for the manufacture of a medicament for the just-mentioned treatment.

The details of one or more embodiments of the invention are set forth in the description below. Other features, objects, and advantages of the invention will be apparent from the description and from the claims.

DETAILED DESCRIPTION

This invention relates to methods of preparing compounds of formula (V). Specifically, these compounds can be prepared by one of the two approaches described below.

An example of the first approach is shown in Scheme 1 below. More specifically, a compound of formula (V) is prepared from a compound of formula (I) via three steps: (1) reacting the compound of formula (I) with $R_1CHO$ (i.e., 2-pyridinecarboxyaldehyde) via an addition-elimination reaction to give a first imine compound, followed by reducing the first imine compound to give a compound of formula (II); (2) reducing the compound of formula (II) to give an aldehyde compound, followed by reacting the aldehyde compound with an amino-protecting agent (i.e., di-tert-butyldicarbonate) to give a compound of formula (III); and (3) reacting the compound of formula (III) with a compound of formula (IV) via another addition-elimination reaction to give a second imine compound, followed by reducing the second imine compound to give the compound of formula (V). If desired, the amino-protecting group $R_2$ on the compound of formula (V) can be removed in a subsequent step.

Scheme 1

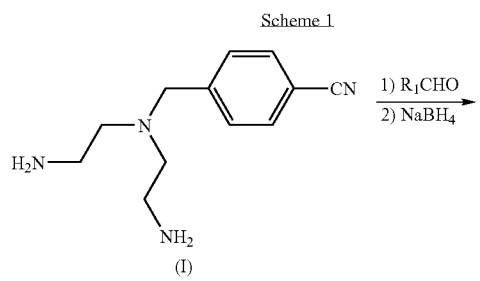

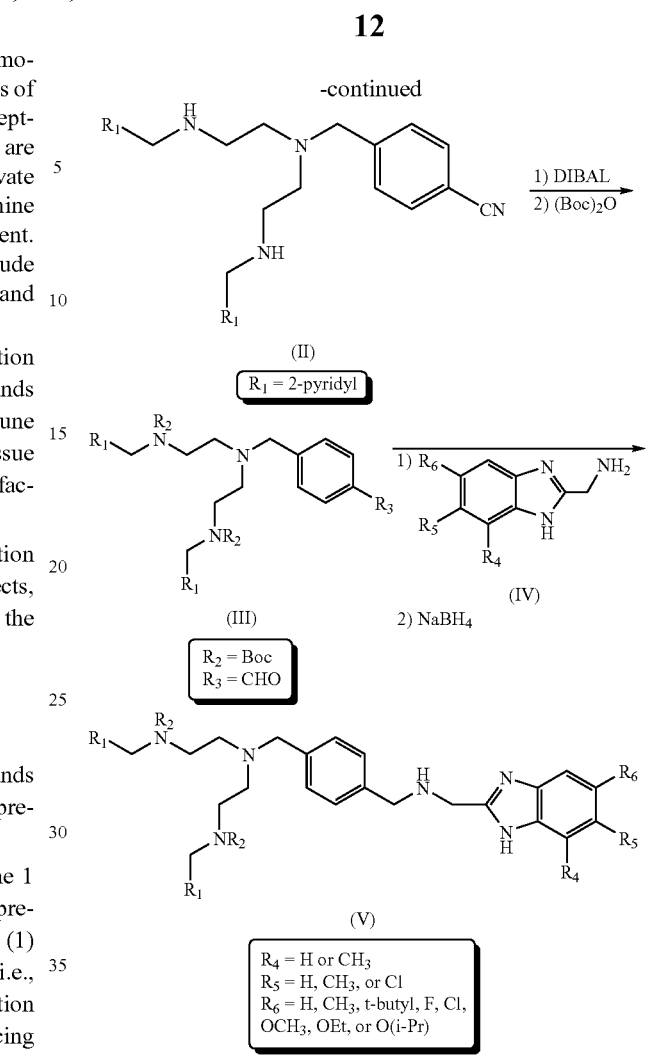

$R_4$ = H or $CH_3$
$R_5$ = H, $CH_3$, or Cl
$R_6$ = H, $CH_3$, t-butyl, F, Cl, $OCH_3$, OEt, or O(i-Pr)

The compound of formula (I) can be prepared by methods known in the art. For example, it can be prepared by first reacting one equivalent amount of diethylenetriamine with two equivalent amounts of an amino-protecting agent to protect the two primary amino groups. The protected diethylenetriamine can then react with 4-cyanobenzyl bromide, followed by removing the amino-protecting groups to give the compound of formula (I). Examples of suitable amino-protecting agents include $(Boc)_2O$, imidazole-Boc, benzyloxycarbonyl chloride, acetyl chloride, phenylcarbonyl chloride, or trialkylsilyl chloride. Exemplary amino-protecting groups include t-butoxycarbonyl, benzyloxycarbonyl, acetyl, phenylcarbonyl, or trialkylsilyl. Other suitable amino-protecting agents and amino-protecting groups, as well as methods of protection and deprotection, have been described in, e.g., T. W. Greene and P. G. M. Wuts, *Protective Groups in Organic Synthesis*, $2^{nd}$ Ed., John Wiley and Sons (1991) and A. J. Pearson and W. R. Roush, *Activating Agents and Protecting Groups*, John Wiley and Sons (1999).

Referring to step (1) mentioned above, the first imine compound can be reduced by any suitable reducing agent. Exemplary reducing agents include hydrogen, zinc and HCl, sodium cyanoborohydride, sodium triacetoxborohydride, sodium boronhydride ($NaBH_4$), sodium borohydride in conjunction with $Ti(Oi-Pr)_4$, borohydride-exchange resin, and formic acid.

Referring to step (2) mentioned above, the aldehyde compound can be prepared from the compound of formula (II), i.e., a nitrile, via a known reduction reaction. For example, the nitrile can be reduced by a metal hydride to add one equivalent of hydrogen and followed by the hydrolysis of the resulting imine. Suitable metal hydrides include LiAlH$_4$, LiAlH(OEt)$_3$, LiAlH(NR$_2$)$_3$, and diisobutylaluminium hydride (DIBAL). As another example, the nitrile can be reduced via the Stephen reduction. Specifically, the nitrile is sequentially treated with HCl and SnCl$_2$ to form an imine, which is subsequently hydrolyzed to form the aldehyde compound. The aldehyde compound thus obtained is then treated with an amino-protecting agent (i.e., (Boc)$_2$O) to protect the two secondary amino groups to form the compound of formula (III).

Referring to step (3) mentioned above, the compound of formula (IV) can be prepared by reacting 1,2-phenylenediamine (in which the phenyl group is optionally substituted) sequentially with chloroacetic acid, sodium azide, and triphenylphosphine. The compound of formula (V) can be prepared from the compound of formula (III) and the compound of formula (IV) in a manner similar to that of the compound of formula (II).

An example of the second approach of preparing a compound of formula (V) is shown in Scheme 2 below. More specifically, a compound of formula (V) is prepared from a compound of formula (II) via two steps: (1) reducing the compound of formula (II) to give a compound of formula (III); and (2) reacting the compound of formula (III) with a compound of formula (VI) in the presence of a base to give the compound of formula (V).

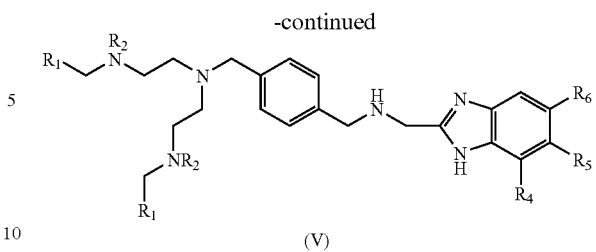

(V)

R$_4$ = H or CH$_3$
R$_5$ = H, CH$_3$, or Cl
R$_6$ = H, CH$_3$, t-butyl, F, Cl, OCH$_3$, OEt, or O(i-Pr)

Referring to the just-mentioned step (1), the compound of formula (II) (i.e., a nitrile) can be reduced to the compound of formula (III) (i.e., an amine) by any suitable reducing agents. Examples of suitable reducing agents include DIBAL, LiAlH$_4$, and BH$_3$—Me$_2$S.

Referring to the just-mentioned step (2), the compound of formula (VI) can be prepared by a known method, such as reacting 1,2-phenylenediamine (in which the phenyl group is optionally substituted) with chloroacetic acid. The compound of formula (V) is subsequently obtained via a nucleophilic substitution reaction between the compound of formula (VI) and the compound of formula (III) obtained in step (1) in the presence of a base (e.g., K$_2$CO$_3$).

A polyamine compound thus synthesized can be further purified by methods such as column chromatography, high-pressure liquid chromatography, or recrystallization.

Other polyamine compounds can be prepared using other suitable starting materials through the synthetic routes set forth above. The methods described above may also include additional steps, either before or after the steps described above, to add or remove suitable protecting groups in order to ultimately allow synthesis of the polyamine compounds. In addition, various synthetic steps may be performed in an alternate sequence or order to give the desired compounds.

Also within the scope of the invention are polyamine compounds of formulas (III) and (V) described in the summary section above. These polyamine compounds can be prepared by the synthetic method disclosed herein, as well as other suitable methods known in the art. The polyamine compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

The polyamine compounds described above can be used for treating an inflammatory or immune disease, a developmental or degenerative disease, or a tissue injury. The term "treating" refers to administering one or more polyamine compounds to a subject, who has an above-described disease, a symptom of such a disease, or a predisposition toward such a disease, with the purpose to confer a therapeutic effect, e.g., to cure, relieve, alter, affect, ameliorate, or prevent the above-described disease, the symptom of it, or the predisposition toward it.

An inflammatory disease is characterized by a local or systemic, acute or chronic inflammation. Examples include inflammatory dermatoses (e.g., dermatitis, eczema, atopic dermatitis, allergic contact dermatitis, urticaria, necrotizing vasculitis, cutaneous vasculitis, hypersensitivity vasculitis, Scheme 2

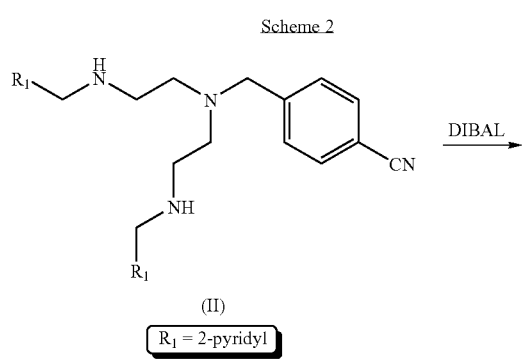

(II)

R$_1$ = 2-pyridyl

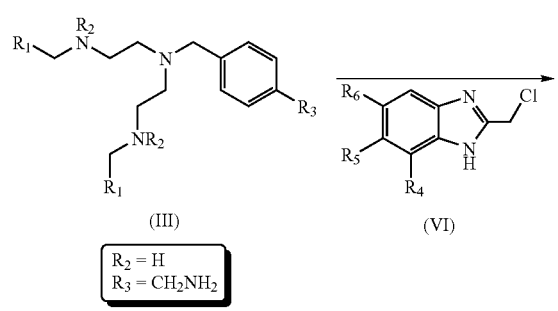

(III)            (VI)

R$_2$ = H
R$_3$ = CH$_2$NH$_2$ eosinophilic myositis, polymyositis, dermatomyositis, and eosinophilic fasciitis), inflammatory bowel diseases (e.g., Crohn's disease and ulcerative colitis), hypersensitivity lung diseases (e.g., hypersensitivity pneumonitis, eosinophilic pneumonia, delayed-type hypersensitivity, interstitial lung disease or ILD, idiopathic pulmonary fibrosis, and ILD associated with rheumatoid arthritis), asthma, and allergic rhinitis.

An immune disease is characterized by a hyper- or hypo-reaction of the immune system. Examples include autoimmune diseases (e.g., rheumatoid arthritis, psoriatic arthritis, systemic lupus erythematosus, myasthenia gravis, juvenile onset diabetes, glomerulonephritis, autoimmune throiditis, ankylosing spondylitis, systemic sclerosis, and multiple sclerosis), acute and chronic inflammatory diseases (e.g., systemic anaphylaxia or hypersensitivity responses, drug allergies, insect sting allergies, graft rejection, including allograft rejection, and graft-versus-host disease), Sjogren's syndrome, human immunodeficiency virus infection, cancer (e.g., brain, breast, prostate, colon, kidney, ovary, thyroid, lung, and haematopoietic cancer), and tumor metastasis.

Developmental diseases are growth or differentiation related disorders that lead to loss-of-function or gain-of-function. Degenerative diseases generally refer to change of a tissue to a lower or less functional form. Examples of a developmental or degenerative disease include spinal muscular atrophy, Duchenne muscular dystrophy, Parkinson's disease, and Alzheimer's disease. Tissue injuries can be caused by oxidative stress (e.g., ischemia-reperfusion in stroke or myocardial infarction), complement activation, graft rejection, chemicals (e.g., alcohol-induced liver damage or mucosal tissue injuries in cancer therapy), viral infection (e.g., glomerular injuries associated with hepatitis C infection), and mechanical forces (e.g., sports injury). Examples of tissue injuries include brain injury, heart injury, liver damage, skeletal muscle injury, kidney damage, pancreatic injury, lung injury, skin injury, and gastrointestinal tract injury.

A subject in need of treatment of an above-described disease can also be concurrently administered with a polyamine compound described above and one or more other therapeutic agents. Examples of such a therapeutic agent include a steroidal or a non-steroidal anti-inflammatory drug, a COX2 inhibitor, a leukotriene receptor inhibitor, a prostaglandin modulator, a TNF modulator, and an immunosuppressive agent (e.g., cyclosporine A). The term "concurrently administered" refers to administering a polyamine compound and one or more other therapeutic agents at the same time or at different times during the period of treatment.

The polyamine compounds described above can be used for enhancing migration of bone marrow-derived cells to blood. The term "bone marrow-derived cells" refers to cells originating from bone marrow. Examples of bone marrow-derived cells include, but are not limited to, CD34+ cells and CD133+ cells.

Also within the scope of this invention is a pharmaceutical composition containing an effective amount of at least one polyamine compound described above and a pharmaceutical acceptable carrier. Further, this invention covers a method of administering an effective amount of one or more of the polyamine compounds to a patient having a disease described in the summary section above. This invention also covers a method of administering an effective amount of one or more of the polyamine compounds for enhancing migration of bone marrow-derived cells to blood. "An effective amount" refers to the amount of an active polyamine compound that is required to confer a therapeutic effect on the treated subject. Effective doses will vary, as recognized by those skilled in the art, depending on the types of diseases treated, route of administration, excipient usage, and the possibility of co-usage with other therapeutic treatment.

A composition having one or more polyamine compounds can be administered to a patient parenterally, orally, nasally, rectally, topically, or buccally. The term "parenteral" as used herein refers to subcutaneous, intracutaneous, intravenous, intrmuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active polyamine compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active polyamine compound. Examples of other carriers include colloidal silicon oxide, magnesium stearate, cellulose, sodium lauryl sulfate, and D&C Yellow # 10.

The polyamine compounds described above can be preliminarily screened for their efficacy in treating above-described diseases by an in vitro assay (See Example 16 below) and then confirmed by animal experiments and clinic trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Preparation of Compound 1: 4-[(bis-{2-[(pyridin-2-ylmethyl)-amino]-ethyl}-amino)-methyl]-benzonitrile Compound 1 was prepared following the procedures described below:

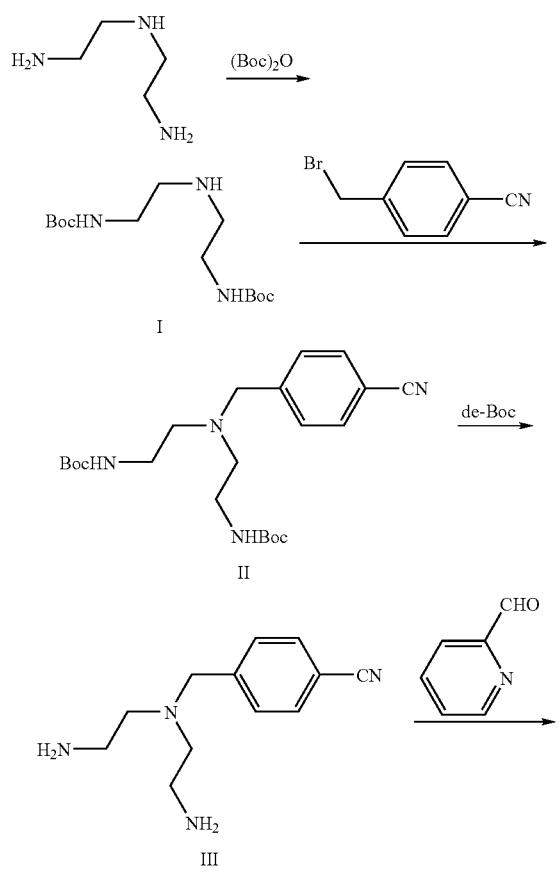

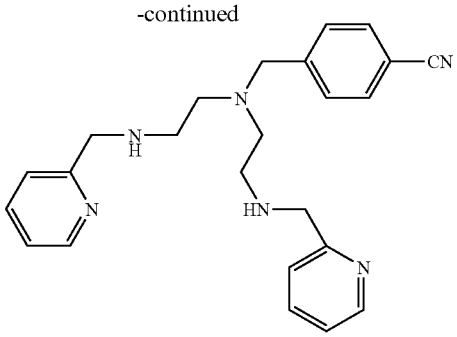

Compound 1

$(Boc)_2O$ (305 g) was added in one batch to a stirred solution of imidazole (100 g) in $CH_2Cl_2$ (500 mL) at room temperature. The reaction mixture was stirred at 25° C. for hours. The solution was then washed with $H_2O$ (200 mL) to remove the imidazole, and subsequently concentrated to give a crude imidazole-Boc (242 g). Diethylenetriamine (68 g) was added in one batch to a stirred solution of the imidazole-Boc (242 g) obtained above in toluene (400 mL) at room temperature. The reaction mixture was heated at 60-65° C. for 3 hours and then concentrated. $CH_2Cl_2$ (400 mL) was added to the above mixture. The solution was then extracted with $H_2O$ (200 mL, 8~10 times) to remove the residual diethylenetriamine. The organic layer was then dried and concentrated to give Intermediate I (202 g) in a 95% yield.

4-Cyanobenzyl bromide (17.3 g) and $K_2CO_3$ (41 g) were added to a stirred solution of Intermediate I (30 g) in acetonitrile (420 mL) at room temperature. The reaction mixture was heated at 60-65° C. for 2 hours. The solution was then filtered and concentrated to give a crude residue. The crude residue was purified by chromatography on silica gel using ethyl acetate and hexane (1:1, v/v) as an eluent to give Intermediate II (30 g) in a 73% yield.

A mixture of 1M HCl/ether (320 mL) was added to a stirred solution of Intermediate II (16 g) in MeOH (160 mL) at room temperature. The reaction mixture was stirred at 25° C. for 15 hours. Diethylether (320 mL) was then added slowly to the mixture to form a precipitate. The precipitate was collected and dried under vacuum to give the hydrochloride salt of Intermediate III (12 g, 95% yield). $H_2O$ (16.4 mL) was added to a stirred mixture of the hydrochloride salt of Intermediate III (12 g) and $K_2CO_3$ (9.86 g) in $CH_3CN$ (640 mL) at room temperature. After the reaction mixture was stirred at 25° C. for 1 hour, $MgSO_4$ (32.8 g) was added and the mixture was stirred for another 1 hour. The solution was then filtered and concentrated to give Intermediate III (6.8 g) in a 85% yield.

2-Pyridinecarboxyaldehyde (7.5 g) was added to a stirred solution of Intermediate III (6.8 g) in MeOH (288 mL) at room temperature. The reaction mixture was heated at 60-65° C. for 2 hour. After the mixture was cooled down to room temperature, $NaBH_4$ (3.45 g, 3.0 equiv.) was slowly added. The mixture was stirred for another 30 minutes, concentrated, quenched with $NH_4Cl$ (aq), and extracted with $CH_2Cl_2$. The combined organic layer was washed with $H_2O$, filtered, and concentrated to give a residue. The residue was purified by chromatography on silica gel (EtOAc/MeOH (1:1) to $NH_4OH$/EtOAc/MeOH (1:5:4), v/v) to afford compound 1 (6 g) in a 70% yield. CI-MS $(M+H^+)$=401.5.

EXAMPLE 2

Preparation of Compound 2: {2-[[2-(tert-butoxycarbonyl-pyridin-2-ylmethyl-amino)-ethyl]-(4-formyl-benzyl)-amino]-ethyl}-pyridin-2-ylmethyl-carbamic acid tert-butyl ester Compound 2 was prepared following the procedures described below:

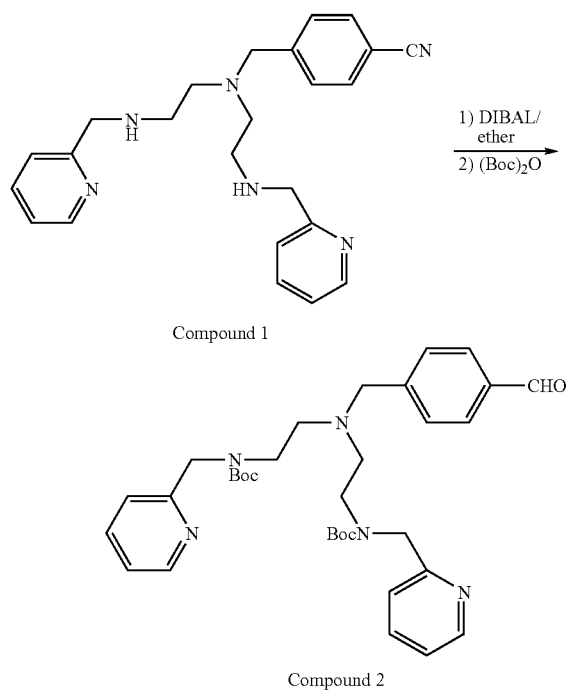

A mixture of 1M DIBAL/ether (66 mL) was added to a stirred solution of compound 1 (4.5 g) in dry toluene (225 g) at −70~−78° C. under $N_2$ (gas). The reaction mixture was stirred at this temperature for 2 hours. After a 5% HCl aqueous solution (66 mL) was added to the above solution at −60~−70° C., the mixture was stirred for another 0.5 hour. The temperature was then allowed to rise from −60° C. to 25° C. KOH (44 g) and $CH_2Cl_2$ (200 mL) were added to the above mixture. The aqueous layer was subsequently extracted with $CH_2Cl_2$ twice. The organic layers were combined and concentrated to give an oil. The oil was dissolved in $CH_2Cl_2$ (120 mL) and $(Boc)_2O$ (4.8 g) was added at room temperature. The solution was stirred at 25° C. for 15 hours and then concentrated to give a crude product. The crude product was purified by chromatography on silica gel using ethyl acetate and hexane (3:2, v/v) as an eluent to afford compound 2 (3.4 g) in a 50% yield. CI-MS $(M+H^+)=604$.

EXAMPLE 3

Preparation of Compound 3: N-(4-aminomethyl-benzyl)-N'-pyridin-2-ylmethyl-N-{2-[(pyridin-2-ylmethyl)-amino]-ethyl}-ethane-1,2-diamine Compound 3 was prepared following the procedures described below:

$LiAlH_4$ (500 mg) was added to a stirred solution of compound 1 (500 mg) in dry THF (60 mL) at 0° C. After stirring for 15 minutes, the solution was cooled to −50° C. and water (50 mL) was added slowly. The mixture was then filtered and extracted with $CH_2Cl_2$. The organic layer was collected and concentrated to give a crude product, which was purified by chromatography on silica gel using $CHCl_3$ as an eluant to afford compound 3 in a 40% yield. CI-MS $(M+H^+)=405$.

EXAMPLE 4

Preparation of Compound 4: N-(4-{[(5-methoxy-1H-benzoimidazol-2-ylmethyl)-amino]-methyl}-benzyl)-N'-pyridin-2-ylmethyl-N-{2-[(pyridin-2-ylmethyl)-amino]-ethyl}-ethane-1,2-diamine Compound 4 was prepared following the procedures described below:

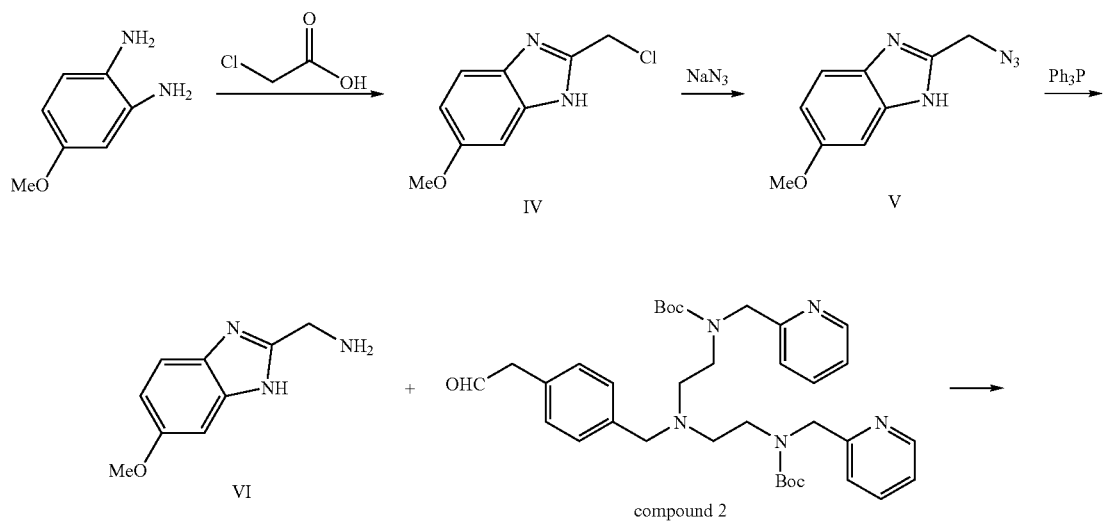

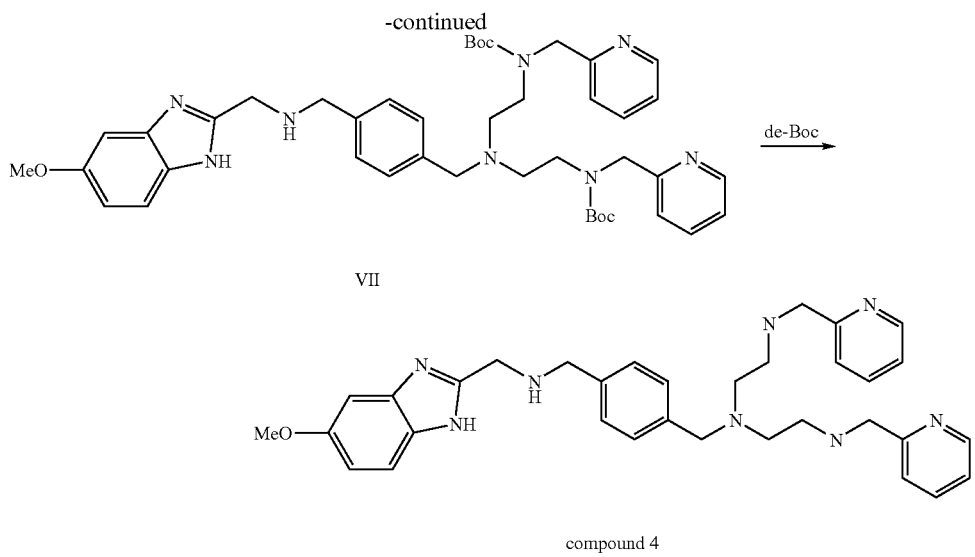

compound 4

Chloroacetic acid (9 g) was added to a stirred solution of 4-methoxy-1,2-phenylenediamine dihydrochloride (10 g) in 40% $H_3PO_4$ (aq) (30 mL) at 100° C. The reaction mixture was stirred at 120° C. for 1 hour. The solution was then diluted with $H_2O$ (200 g) and the pH was adjusted from 1 to 8 by $K_2CO_3$ (20 g). The solution was subsequently extracted with EtOAc (200 mL). The organic layer was collected and concentrated to give crude Intermediate IV, 2-(methylchloride)-6-methoxy-benzimidazole (75 g).

Sodium azide (8.8 g) was added to crude Intermediate IV (75 g) in EtOH (200 mL) at room temperature. The reaction mixture was heated at 80° C. for 4 hours. The solution was then concentrated to give a residue. The residue was purified by chromatography on silica gel using ethyl acetate and hexane (3:2, v/v) as an eluent to give Intermediate V, 2-(methylazide)-6-methoxy-benzimidazole (7.3 g) in a 78% yield.

Triphenylphosphine (18.8 g) and $H_2O$ (0.7 g) were added to a stirred solution of Intermeidate V (7.3 g) in THF (300 mL) at room temperature. The reaction mixture was stirred at 25° C. for 15 hours and then concentrated to give a residue. The residue was purified by chromatography on silica gel using triethylamine/EtOAc/MeOH (1:5:4, v/v) as an eluent to give Intermediate VI, 2-(aminomethyl)-6-methoxy-benzimidazole (5.7 g) in a 90% yield.

A solution of Intermediate VI (5.7 g) and compound 2 (8.4 g) in $CH_3OH$ (420 mL) was heated at 60° C. for 6 hours. After the solution was cooled down to room temperature, $NaBH_4$ (1 g) was added to it slowly. The mixture was stirred for another 30 minutes. Subsequently, the mixture was concentrated, quenched with $NH_4Cl$ (aq), and extracted with $CH_2Cl_2$. The organic layer was collected and concentrated to give a residue, which was purified by chromatography on silica gel (EtOAc/MeOH (9:1, v/v)) to give Intermediate VII (7.5 g) in a 70% yield.

A mixture of 1M HCl/ether (150 mL) was added to a stirred solution of Intermediate VII (7.5 g) in MeOH (75 mL) at room temperature. After the reaction mixture was stirred at 25° C. for 15 hours, it was concentrated to give a solid. The solid was dried under high vacuum to give crude hydrochloride salt of compound 4 (6.8 g) in a 85% yield. IPA (100 mL) was added slowly to a stirred solution of the crude hydrochloride salt of compound 4 (6.8 g) in MeOH (50 ml) at 65° C. and the seeding was developed at 50° C. Subsequently, the temperature was kept at 40~45° C. for 2 hours and then at 25° C. for another 2 hours. The hydrochloride salt of compound 4 (5.5 g, recovery yield: 80%) was obtained by filtration and then dried under high vacuum (<1 torr) at 50° C. for 15 hours. CI-MS $(M+H^+)$=565.

EXAMPLE 5

Preparation of Compound 5: N-(4-{[(1H-benzoimidazol-2-ylmethyl)-amino]-methyl}-benzyl)-N'- pyridin-2-ylmethyl-N-{2-[(pyridin-2-ylmethyl)-amino]-ethyl}-ethane-1,2-diamine Compound 5 was prepared in a manner similar to that described in Example 4.
CI-MS $(M+H^+)$=535.

EXAMPLE 6

Preparation of Compound 6: N-(4-{[(5-methyl-1H-benzoimidazol-2-ylmethyl)-amino ]-methyl}-benzyl)-N'-pyridin-2-ylmethyl-N-{2-[(pyridin-2-ylmethyl)-amino ]-ethyl}-ethane-1,2-diamine Compound 6 was prepared in a manner similar to that described in Example 4.
CI-MS $(M+H^+)$=549.

EXAMPLE 7

Preparation of Compound 7: N-(4-{[(5-fluoro-1H-benzoimidazol-2-ylmethyl)-amino ]-methyl}-benzyl)-N'-pyridin-2-ylmethyl-N-{2-[(pyridin-2-ylmethyl)-amino ]-ethyl}-ethane-1,2-diamine Compound 7 was prepared in a manner similar to that described in Example 4.
CI-MS $(M+H^+)$=553.5.

EXAMPLE 8

Preparation of Compound 8: N-(4-{[(5-chloro-1H-benzoimidazol-2-ylmethyl)-amino ]-methyl}-benzyl)-N'-pyridin-2-ylmethyl-N-{2-[(pyridin-2-ylmethyl)-amino ]-ethyl}-ethane-1,2-diamine Compound 8 was prepared in a manner similar to that described in Example 4.
CI-MS (M+H$^+$)=570.

EXAMPLE 9

Preparation of Compound 9: N-(4-{[(7-methyl-1H-benzoimidazol-2-ylmethyl)-amino ]-methyl}-benzyl)-N'-pyridin-2-ylmethyl-N-{2-[(pyridin-2-ylmethyl)-amino ]-ethyl}-ethane-1,2-diamine Compound 9 was prepared in a manner similar to that described in Example 4.
CI-MS (M+H$^+$)=549.

EXAMPLE 10

Preparation of Compound 10: N-(4-{[(5-ethoxy-1H-benzoimidazol-2-ylmethyl)-amino ]-methyl}-benzyl)-N'-pyridin-2-ylmethyl-N-{2-[(pyridin-2-ylmethyl)-amino ]-ethyl}-ethane-1,2-diamine Compound 10 was prepared in a manner similar to that described in Example 4.
CI-MS (M+H$^+$)=579.

EXAMPLE 11

Preparation of Compound 11: N-(4-{[(5,6-dimethyl-1H-benzoimidazol-2-ylmethyl)-amino ]-methyl}-benzyl)-N'-pyridin-2-ylmethyl-N-{2-[(pyridin-2-ylmethyl)-amino ]-ethyl}-ethane-1,2-diamine Compound 11 was prepared in a manner similar to that described in Example 4.
Ci-MS (M+H$^+$)=563.

EXAMPLE 12

Preparation of Compound 12: N-(4-{[(6-chloro-5-methyl-1H-benzoimidazol-2-ylmethyl)-amino ]-methyl}-benzyl)-N'-pyridin-2-ylmethyl-N-{2- [(pyridin-2-ylmethyl)-amino]-ethyl}-ethane-1,2-diamine Compound 12 was prepared in a manner similar to that described in Example 4.
CI-MS (M+H$^+$)=584.

EXAMPLE 13

Preparation of Compound 13: N-(4-{[(5-isopropoxy-1H-benzoimidazol-2-ylmethyl)-amino ]-methyl}-benzyl)-N'-pyridin-2-ylmethyl-N-{2-[(pyridin-2-ylmethyl)-amino ]-ethyl}-ethane-1,2-diamine Compound 13 was prepared in a manner similar to that described in Example 4.
CI-MS (M+H$^+$)=593.8.

EXAMPLE 14

Preparation of Compound 14: N-(4-{[(5-tert-butyl-1H-benzoimidazol-2-ylmethyl)-amino ]-methyl}-benzyl)-N'-pyridin-2-ylmethyl-N-{2-[(pyridin-2-ylmethyl)-amino ]-ethyl}-ethane-1,2-diamine Compound 14 was prepared in a manner similar to that described in Example 4.
CI-MS (M+H$^+$)=591.5.

EXAMPLE 15

Preparation of Compound 15: N-(4-{[(5,6-dichloro-1H-benzoimidazol-2-ylmethyl)-amino ]-methyl}-benzyl)-N'-pyridin-2-ylmethyl-N-{2-[(pyridin-2-ylmethyl)-amino ]-ethyl}-ethane-1,2-diamine Compound 15 was prepared in a manner similar to that described in Example 4.
CI-MS (M+H$^+$)=604.5.

EXAMPLE 16

In vitro Assay

Compounds 4-15 were tested for their efficacy in binding to CXCR4 receptor using a DELFIA GTP-binding kit (Wallac Oy, Turku, Finland). The DELFIA GTP-binding assay is a time-resolved fluorometric assay based on GDP-GTP exchange on G-protein subunits followed by activation of a G protein-coupled receptor by its agonists. Eu-GTP, obtained from Wallac Oy, was used in this assay to allow monitoring of agonist-dependent activation of G-protein. Stimulation of CXCR4 receptor by SDF-1 leads to the replacement of GDP by GTP on the α-subunit of G-protein. This GTP-Gα complex represents the activated form of G-protein. Eu-GTP, a non-hydrolysable analog of GTP, can be used to quantify the amount of activated G-protein. (Peltonen et al., Eur. J. Pharmacol. (1998) 355:275.)

Plasma membrane of CXCR4-expressing HEK293 cells was suspended in an assay buffer (50 mM NaCl, 100 μg/mL saponin, 3 mM MgCl$_2$, 3 μM GDP, 5% BSA, 50 mM HEPES, pH 7.4). An aliquot (4 μg protein) was added to each well of an AcroPlate (Pall Life Sciences, Ann Arbor, Mich.). After the addition of the test compounds (10 μM in 0.1% DMSO) and stromal-derived factor-1 (4 nM in the assay buffer), the assay plate was incubated in the dark at room temperature with slow shaking for 10 minutes. Eu-GTP was added to each well and the plate was incubated again for 60 minutes. The assay was terminated by washing the plate twice with a wash solution provided in the assay kit. Binding of Eu-GTP was determined based on the fluorescence signal from a Victor 2 multi-label reader.

Unexpectedly, all test compounds showed IC$_{50}$ values in the range of 13-48 mM.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of formula (V):

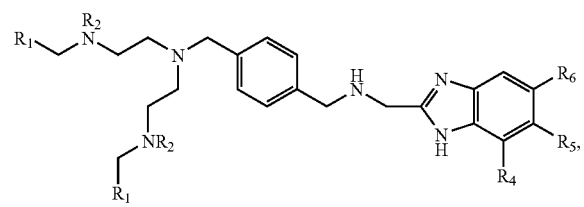

(V)

wherein

R$_1$ is heteroaryl, aryl, C$_3$-C$_8$ cycloalkyl, or C$_3$-C$_8$ heterocycloalkyl;

R$_2$ is H or an amino-protecting group; and each of R$_4$, R$_5$, and R$_6$, independently, is H, OR', halogen, C$_1$-C$_{10}$ alkyl, C$_3$-C$_8$ cycloalkyl, C$_3$-C$_8$ heterocycloalkyl, heteroaryl, or aryl; in which R' is H, C$_1$-C$_{10}$ alkyl, C$_3$-C$_8$ cycloalkyl, C$_3$-C$_8$ heterocycloalkyl, aryl, or heteroaryl; at most two of R$_4$, R$_5$, and R$_6$ being H.

2. The compound of claim 1, wherein R$_1$ is heteroaryl.

3. The compound of claim 2, wherein R$_1$ is pyridyl.

4. The compound of claim 3, wherein R$_2$ is H, t-butoxycarbonyl, benzyloxycarbonyl, acetyl, phenylcarbonyl, or trialkylsilyl.

5. The compound of claim 4, wherein each of R$_4$, R$_5$, and R$_6$ is H, OR', or halogen.

6. The compound of claim 5, wherein the compound is one of

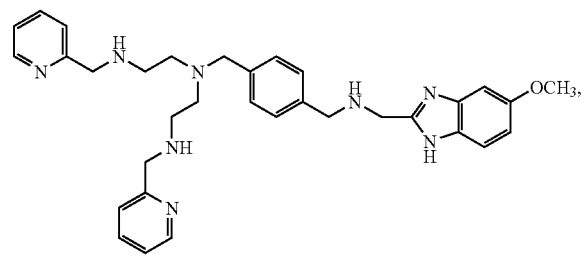

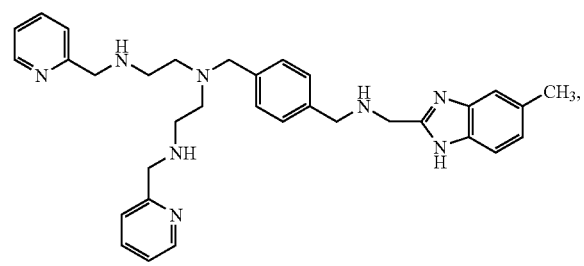

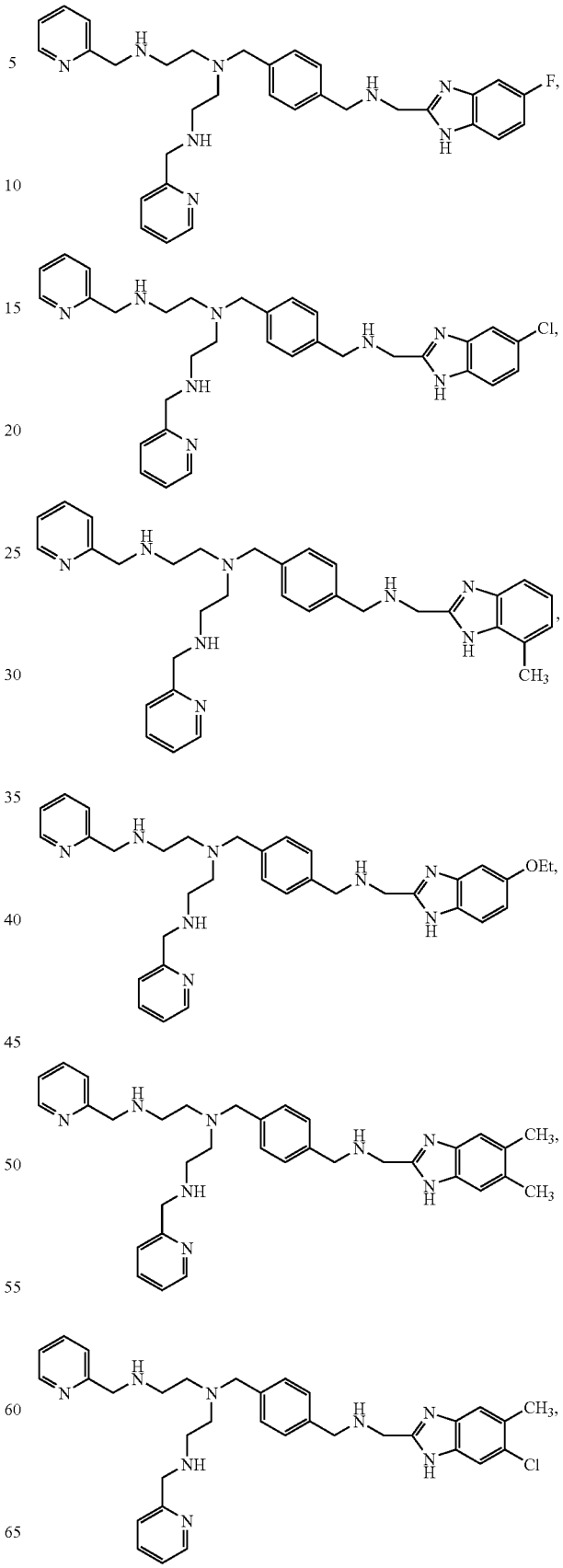

-continued

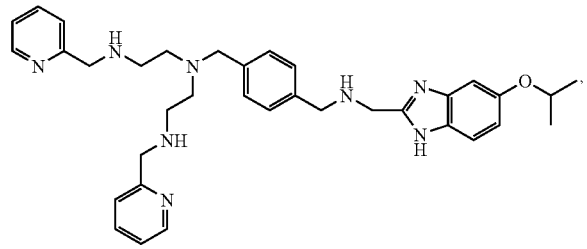

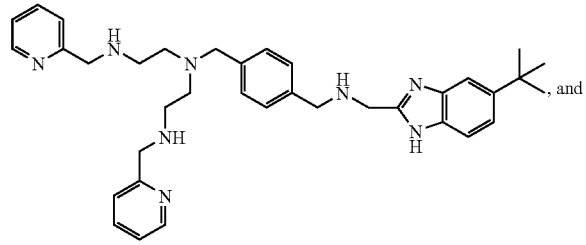

, and

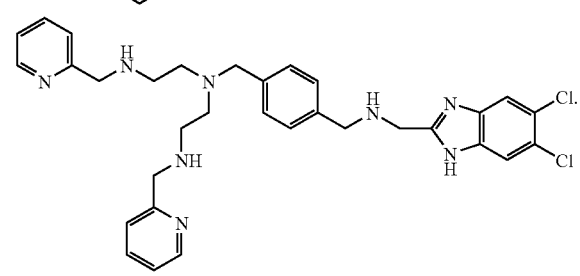

7. The compound of claim 1, wherein $R_2$ is H, t-butoxycarbonyl, benzyloxycarbonyl, acetyl, phenylcarbonyl, or trialkylsilyl.

8. The compound of claim 7, wherein each of $R_4$, $R_5$, and $R_6$ is H, OR', or halogen.

9. A chemical synthetic method, comprising reacting a compound of formula (III):

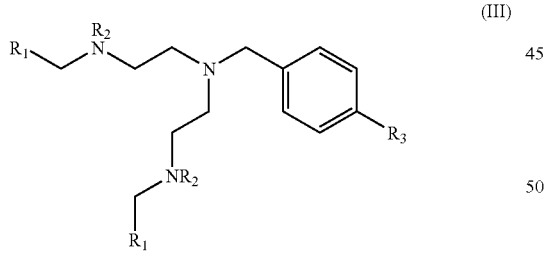

(III)

with a compound of formula (IV):

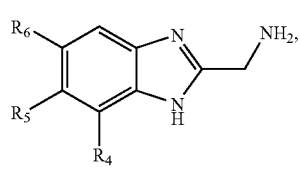

(IV)

to give an imine compound, followed by reducing the imine compound to give a compound of formula (V):

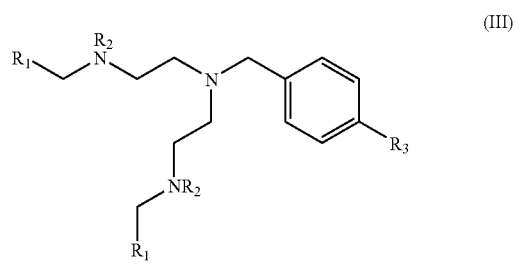

(V)

wherein $R_1$ is heteroaryl, aryl, $C_3$-$C_8$ cycloalkyl, or $C_3$-$C_8$ heterocycloalkyl; $R_2$ is an amino-protecting group; $R_3$ is C(O)H; and each of $R_4$, $R_5$, and $R_6$, independently, is H, OR', halogen, $C_1$-$C_{10}$ alkyl, $C_3$-$C_8$ cycloalkyl, $C_3$-$C_8$ heterocycloalkyl, aryl, or heteroaryl; in which R' is H, $C_1$-$C_{10}$ alkyl, $C_3$-$C_8$ cycloalkyl, $C_3$-$C_8$ heterocycloalkyl, aryl, or heteroaryl; at most two of $R_4$, $R_5$, and $R_6$ being H.

10. The method of claim 9, further comprising removing the protecting group $R_2$.

11. A chemical synthetic method, comprising reacting a compound of formula (III):

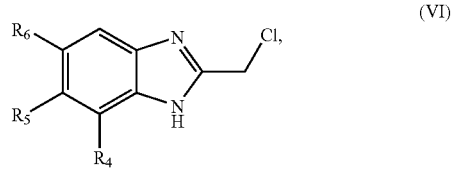

(III)

with a compound of formula (VI):

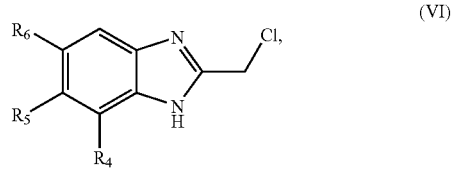

(VI)

to give a compound of formula (V):

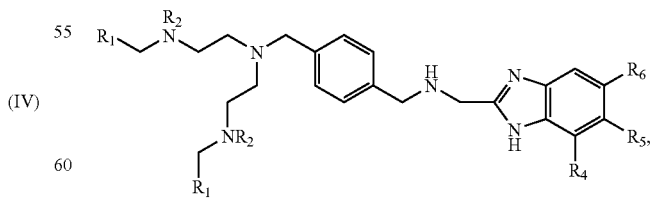

(V)

wherein $R_1$ is heteroaryl, aryl, $C_3$-$C_8$ cycloalkyl, or $C_3$-$C_8$ heterocycloalkyl; $R_2$ is H; $R_3$ is $CH_2NH_2$; and each of $R_4$, $R_5$, and $R_6$, independently, is H, OR', halogen, $C_1$-$C_{10}$ alkyl, $C_3$-$C_8$ cycloalkyl, $C_3$-$C_8$ heterocycloalkyl, heteroaryl, or aryl;

in which R' is H, $C_1$-$C_{10}$ alkyl, $C_3$-$C_8$ cycloalkyl, $C_3$-$C_8$ heterocycloalkyl, aryl, or heteroaryl; at most two of $R_1$, $R_5$, and $R_6$ being H.

12. The method of claim 9, further comprising reacting a compound of formula (I):

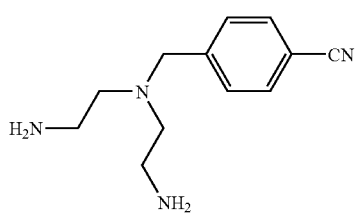

with $R_1CHO$ to give a first imine compound, followed by reducing the first imine compound to give a compound of formula (II):

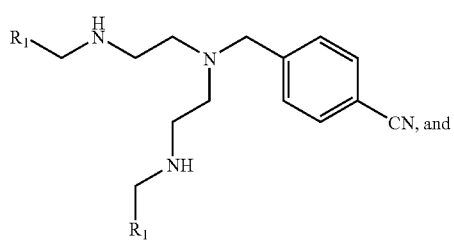

reducing the compound of formula (II) to give an aldehyde compound, followed by reacting the aldehyde compound with an amino-protecting agent to give the compound of formula (III).

13. The method of claim 12, wherein $R_1$ is heteroaryl.

14. The method of claim 13, wherein $R_1$ is pyridyl.

15. The method of claim 14, wherein $R_2$ is t-butoxycarbonyl, benzyloxycarbonyl, acetyl, phenylcarbonyl, or trialkylsilyl.

16. The method of claim 12, further comprising removing the protecting group $R_2$.

17. The method of claim 11, further comprising reacting a compound of formula (I):

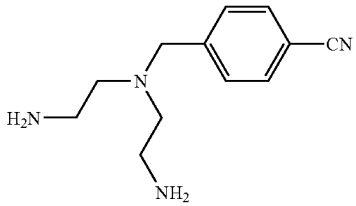

with $R_1CHO$ to give a first imine compound, followed by reducing the first imine compound to give a compound of formula (II):

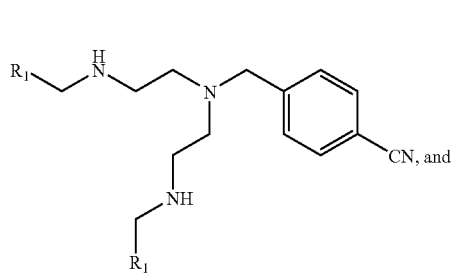

reducing the compound of formula (II) to give the compound of formula (III).

18. The method of claim 17, wherein $R_1$ is heteroaryl.

19. The method of claim 18, wherein $R_1$ is pyridyl.

* * * * *